(12) United States Patent
Campin et al.

(10) Patent No.: US 7,044,944 B2
(45) Date of Patent: *May 16, 2006

(54) OPTIMIZATION OF ABLATION CORRECTION OF AN OPTICAL SYSTEM AND ASSOCIATED METHODS

(75) Inventors: John Alfred Campin, Orlando, FL (US); George H. Pettit, Maitland, FL (US)

(73) Assignee: Alcon RefractiveHorizons, Inc., Fort Worth, TX (US)

( * ) Notice: Subject to any disclaimer, the term of this patent is extended or adjusted under 35 U.S.C. 154(b) by 241 days.

This patent is subject to a terminal disclaimer.

(21) Appl. No.: 10/238,919

(22) Filed: Sep. 10, 2002

(65) Prior Publication Data

US 2003/0078753 A1    Apr. 24, 2003

Related U.S. Application Data

(63) Continuation-in-part of application No. 09/814,398, filed on Mar. 22, 2001, now Pat. No. 6,569,154.

(60) Provisional application No. 60/348,586, filed on Jan. 14, 2002, provisional application No. 60/191,187, filed on Mar. 22, 2000.

(51) Int. Cl.
   *A91B 18/18*    (2006.01)
(52) U.S. Cl. ................ 606/5; 606/4; 606/10; 351/212; 128/898
(58) Field of Classification Search .................... 606/4, 606/5, 10–12; 351/208–212; 128/898
   See application file for complete search history.

(56) References Cited

U.S. PATENT DOCUMENTS

| | | | |
|---|---|---|---|
| 4,420,228 A | 12/1983 | Humphrey | |
| 4,669,466 A | 6/1987 | L'Esperance | |
| 4,688,941 A | 8/1987 | Philbert | |
| 4,750,818 A | 6/1988 | Cochran | |
| 5,106,183 A | 4/1992 | Yoder, Jr. | |
| 5,221,834 A | 6/1993 | Lisson et al. | |
| 5,233,174 A | 8/1993 | Zmek | |
| 5,339,121 A | 8/1994 | Shimmick et al. | |
| 5,452,031 A | 9/1995 | Ducharme | |

(Continued)

FOREIGN PATENT DOCUMENTS

WO    WO 98/53881    12/1998

(Continued)

OTHER PUBLICATIONS

Liang, et al., "Objective Measurement of Wave Aberrations of the Human Eye with the Use of a Hartmann-Shack Wave-front Sensor," *J. Opt. Soc. Am. A*, vol. 11, No. 7, Jul. 1994, pp. 1949-1957.

(Continued)

*Primary Examiner*—Ahmed Farah
(74) *Attorney, Agent, or Firm*—Allen, Dyer, Doppelt, Milbrath & Gilchrist, P.A.

(57) ABSTRACT

A system and method for converting measured wavefront data into an ablation profile for correcting visual defects includes providing measured wavefront data on an aberrated eye by a method such as known in the art. The measured wavefront data are correlated with accumulated data on previously treated eyes. Next an adjustment is applied to the measured wavefront data based upon the correlating step. This adjustment is used to form adjusted wavefront data for input to a wavefront data correction algorithm to calculate an ablation profile therefrom. The wavefront data correction algorithm may be modeled as, for example, Zernike polynomials with adjusted coefficients.

21 Claims, 12 Drawing Sheets

U.S. PATENT DOCUMENTS

| | | | |
|---|---|---|---|
| 5,493,391 A | 2/1996 | Neal et al. | |
| 5,632,742 A | 5/1997 | Frey et al. | |
| 5,684,545 A | 11/1997 | Dou et al. | |
| 5,777,719 A * | 7/1998 | Williams et al. | 351/212 |
| 5,782,822 A * | 7/1998 | Telfair et al. | 606/5 |
| 5,822,035 A | 10/1998 | Bille | |
| 5,841,511 A | 11/1998 | D'Souza et al. | |
| 5,849,006 A | 12/1998 | Frey et al. | |
| 5,949,521 A | 9/1999 | Williams et al. | |
| 6,095,651 A | 8/2000 | Williams et al. | |
| 6,129,722 A * | 10/2000 | Ruiz | 606/5 |
| 6,245,059 B1 | 6/2001 | Clapham | |
| 6,271,915 B1 | 8/2001 | Frey et al. | |
| 6,280,435 B1 | 8/2001 | Odrich et al. | |
| 6,322,216 B1 | 11/2001 | Yee et al. | |
| 6,413,251 B1 | 7/2002 | Williams | |
| 6,460,997 B1 | 10/2002 | Frey et al. | |

FOREIGN PATENT DOCUMENTS

| | | |
|---|---|---|
| WO | WO 99/27334 | 6/1999 |

OTHER PUBLICATIONS

Roberts, "Characterization of the Inherent Error in a Spherically-Biased Corneal Topography System in Mapping a Radially Aspheric Surface," *Journal of Refractive & Corneal Surgery*, vol. 10, Mar./Apr. 1994, pp. 103-111.

Charman, "Wavefront Aberration of the Eye: A Review," *Optometry and Vision Science*, vol. 68, No. 8, pp. 574-583.

Gauthier, et al., "Factors Affecting Epithelial Hyperplasia After Photorefractive Keratectomy," *J Cataract Refract Surgery*, vol. 23, Sep. 1991, pp. 1042-1050.

Förster, MD, et al., "Steep Central Islands After Myopic Photorefractive Keratectomy," *J Cataract Refract Surgery*, vol. 24, Jul. 1998, pp. 899-904.

Munnerlyn, Ph.D., et al., "Photorefractive Keratectomy: A Technique for Laser Refractive Surgery" *J Cataract Refract Surgery*, vol. 14, Jan. 1988, pp. 46-52.

Wilson, "Structure of the Corneal Stroma," *Vision Res.*, vol. 10, Oct. 1969, pp. 519-520.

Vinciguerra, et al., "Photorefractive Keratoplasty I," Investigative Ophthamology & Visual Science, vol. 36, No. 4, pp. 81.

Jim Schwiegerling and John E. Greivenkamp, "Using Corneal Height Maps and Polynomial Decomposition to Determine Corneal Aberrations", Optometry and Vision Science, vol. 74, No. 11, pp. 906-916, Nov. 1997.

Peter Mierdel, Maik Kaemmerer, Hans-Eberhard Krinke, and Theo Seiler, "Effects of Photorefractive Keratectomy And Cataract Surgery On Ocular Optical Errors Of Higher Order," Graefe's Arch Clin., Exp Ophthalmol, 237:725-729, Mar. 1999.

* cited by examiner

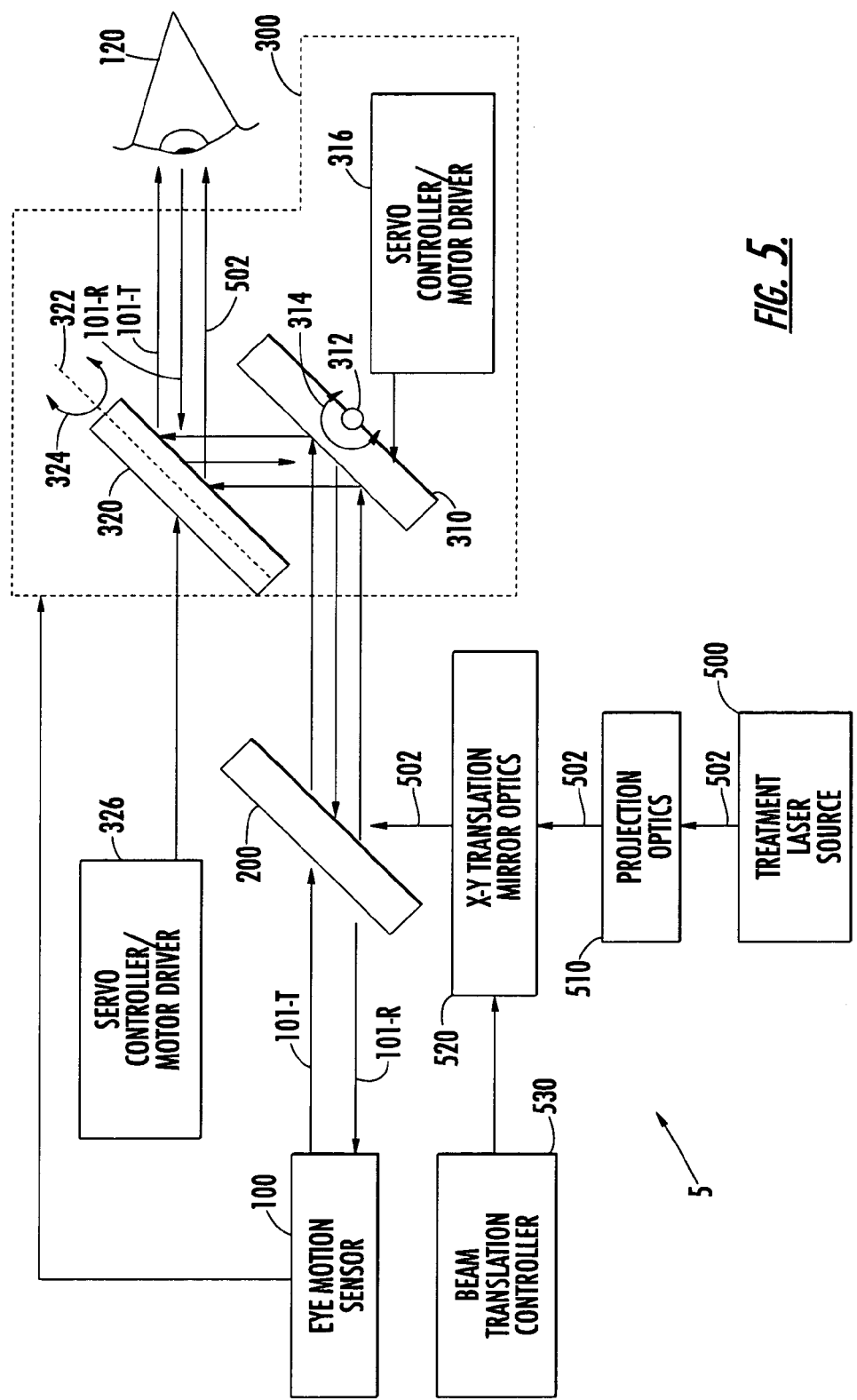

OPTIMIZATION OF ABLATION CORRECTION OF AN OPTICAL SYSTEM AND ASSOCIATED METHODS

CROSS-REFERENCE TO RELATED APPLICATION

This application claims priority to provisional application Ser. No. 60/348,586, filed Jan. 14, 2002, for "Myopic Wavefront Treatment Optimization," and also continuation-in-part to application Ser. No. 09/814,398, filed Mar. 22, 2001, now U.S. Pat. No. 6,569,154, for "Optimization of Ablation Correction of an Optical System and Associated Methods," which itself claims priority to provisional application Ser. No. 60/191,187, filed Mar. 22, 2000, for "Optimizing Refractive Surgery Ablation Profiles by Compensating for Ablation Effectiveness Function," all of which are commonly owned with the present invention and which are incorporated herein by reference.

BACKGROUND OF THE INVENTION

1. Field of the Invention

The present invention relates to optical aberration measurement and correction, and, more particularly, to a system and method for achieving an empirical, global optimization of an objective measurement and correction of an optical system such as the human eye.

2. Description of Related Art

Optical systems having a real image focus can receive collimated light and focus it at a point. Such optical systems can be found in nature, e.g., human and animal eyes, or can be manmade, e.g., laboratory systems, guidance systems, and the like. In either case, aberrations in the optical system can affect the system's performance.

A perfect or ideal human eye diffusely reflects an impinging light beam from its retina through optics of the eye, which includes a lens and a cornea. For such an ideal eye in a relaxed state, i.e., not accommodating to provide near-field focus, reflected light exits the eye as a sequence of plane waves. However, a real eye typically has aberrations that cause deformation or distortion of reflected light waves exiting the eye. An aberrated eye diffusely reflects an impinging light beam from its retina through its lens and cornea as a sequence of distorted wavefronts.

It is known in the art to perform laser correction of focusing deficiencies by photorefractive keratectomy (PRK), which modifies corneal curvature, and LASIK surgery. Such methods typically employ a 193-nm excimer laser to ablate corneal tissue. Munnerlyn et al. (*J. Cataract Refract. Surg.* 14(1), 46–52, 1988) have presented equations for determining a specific volume of tissue to be removed to achieve a desired refractive correction. Frey (U.S. Pat. No. 5,849,006) teaches a method of using a small-spot laser to remove a desired volume of tissue for effecting a desired refractive correction.

In U.S. application Ser. No. 09/566,668, filed May 8, 2000, for "Apparatus and Method for Objective Measurement and Correction of Optical Systems Using Wavefront Analysis," commonly owned with the present application, the disclosure of which is incorporated herein by reference, it is taught to use Zernike polynomials to approximate a distorted wavefront emanating from an aberrated eye. In this approach a wavefront $W(x,y)$ is expressed as a weighted sum of individual polynomials, with i running from 0 to n, of $C_i Z_i(x,y)$, where the $C_i$ are the weighting coefficients and the $Z_i(x,y)$ are the Zernike polynomials up to some order. As illustrated in FIG. 8A, a pre-operatively measured wavefront 70 is treated with an algorithm 71 to form a treatment profile 72, which is then transmitted to a corneal ablation system for treating the aberrated eye.

SUMMARY OF THE INVENTION

The present invention includes a first embodiment comprising an optical correction system for correcting visual defects of an eye. The system comprises a wavefront analyzer responsive to a wavefront emanating from an eye for determining an optical path difference between a reference wave and the wavefront. The system further comprises a converter for providing an optical correction based on the path difference and on a radially dependent ablation efficiency. The efficiency correction uses a compensating polynomial of the form $A+B\rho+C\rho^2+D\rho^3+\ldots+X\rho^n$, where $\rho$ is a normalized radius that is optical zone specific and is measured from a central portion of the cornea, reaching a value of 1 at the edge of the optical correction zone, and n is the highest-order polynomial used in order to accurately describe the radial efficiency.

A laser beam is directed to the cornea with sufficient power to ablate corneal material. The optical correction is achieved by the removal of a selected amount of the corneal material to create a desired corneal shape change based on the optical correction.

A second embodiment of the invention is directed to a method for converting measured wavefront data into an ablation profile for correcting visual defects. The method comprises the steps of providing measured wavefront data on an aberrated eye by a method such as known in the art. The measured wavefront data are correlated with accumulated data on previously treated eyes. Next an adjustment is applied to the measured wavefront data based upon the correlating step. This adjustment is used to form adjusted wavefront data for input to a wavefront data correction algorithm to calculate an ablation profile therefrom. The wavefront data correction algorithm may comprise, for example, the Zernike polynomials as previously disclosed, although this is not intended as a limitation.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 4A plots $1-0.3r^2$, where $r_{max}=3.25$ mm; FIG. 4B plots $0.95-0.3r^2-0.25r^3+0.3r^4$.

FIG. 5 is a schematic diagram of a system for delivering an ablative laser beam to an eye.

DETAILED DESCRIPTION OF THE PREFERRED EMBODIMENTS

Figure 1:
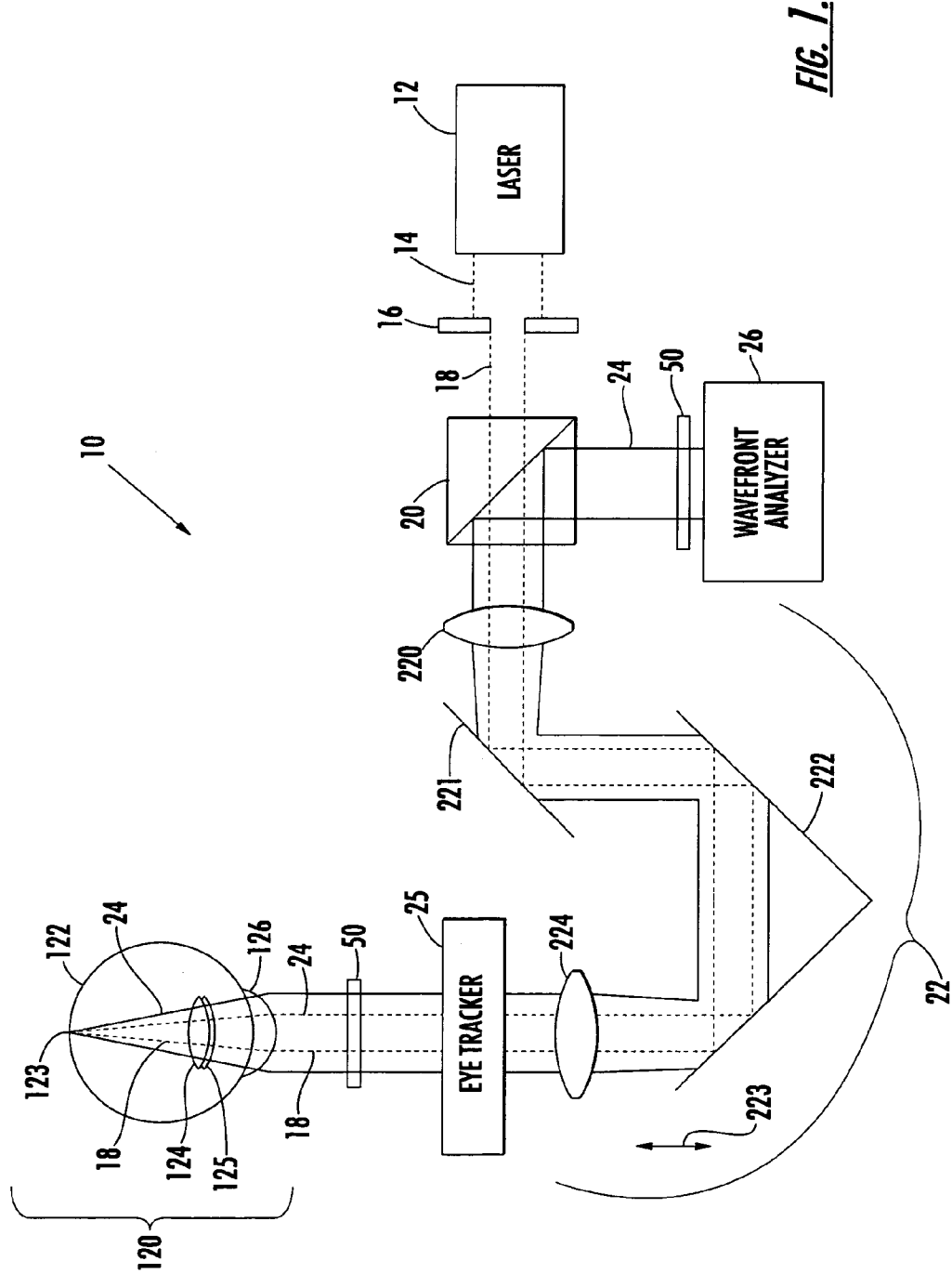
FIG. 1 is a schematic diagram of a system for determining ocular aberrations.
Figure 2:
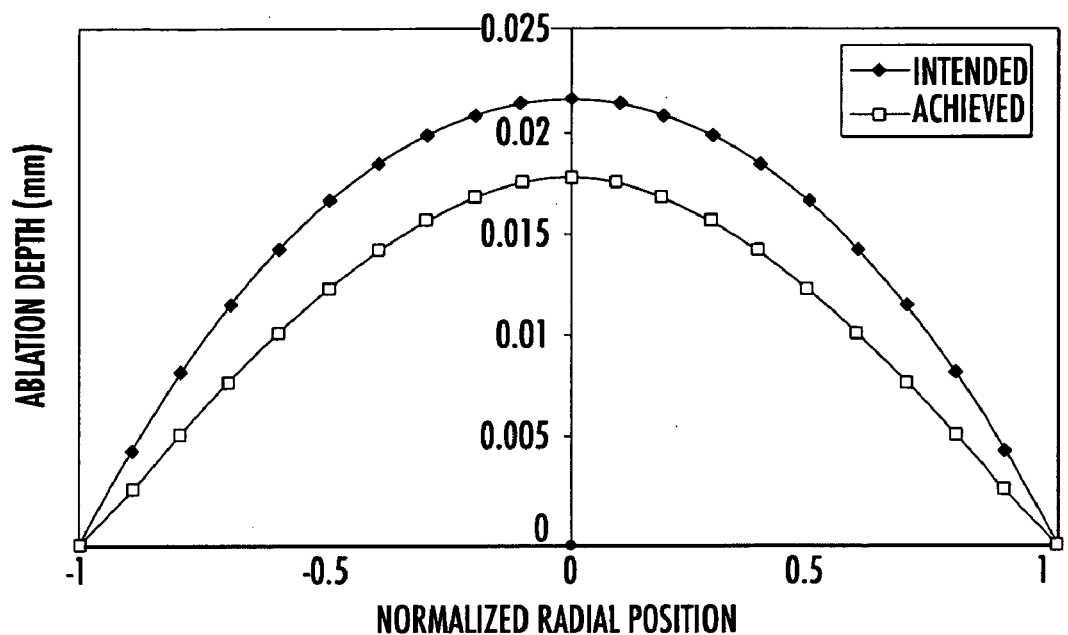
FIG. 2 is a graph of desired and achieved ablation depths as a function of radial position for a myopic eye.
Figure 3:
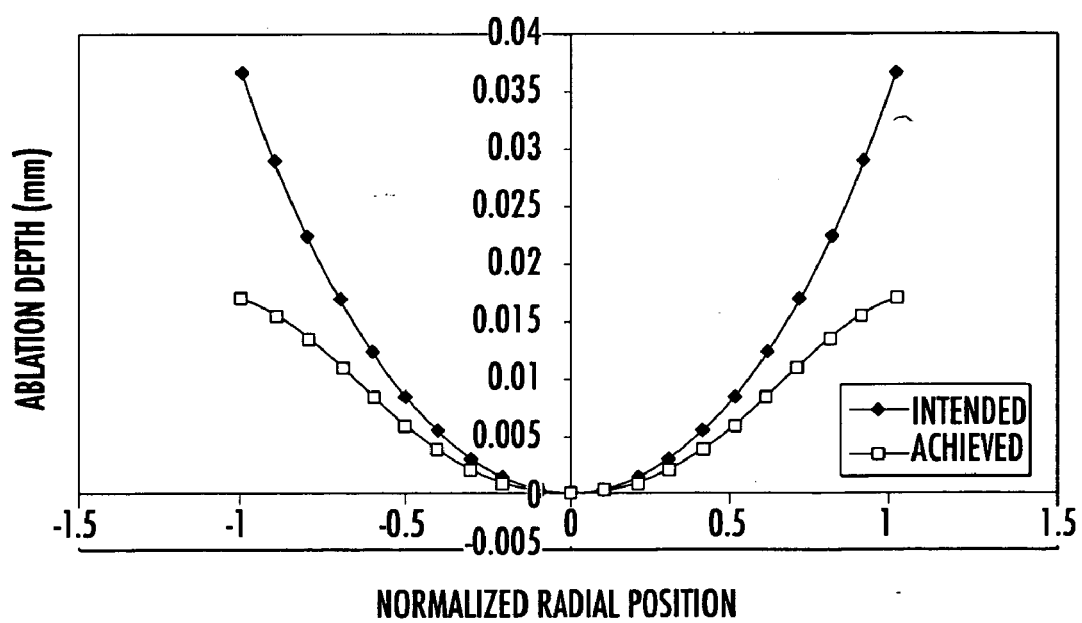
FIG. 3 is a graph of desired and achieved ablation depths as a function of radial position for a hyperopic eye.

A description of the preferred embodiments of the present invention will now be presented with reference to FIGS. 1–15.

The system and method for correcting visual defects of an eye includes a wavefront analyzer, in a preferred embodiment a system 10 (FIG. 1) similar to that described in copending and co-owned application Ser. No. 09/664,128, the contents of which are incorporated herein by reference. The apparatus 10 includes a laser 12 for generating optical radiation used to produce a small-diameter laser beam 14. The laser 12 generates a collimated laser light beam (represented by dashed lines for the beam 14) of a wavelength and power that is eye-safe. For ophthalmic applications, appropriate wavelengths would include the entire visible spectrum and the near-infrared spectrum. By way of example, appropriate wavelengths may be in a range of from approximately 400–1000 nms, including 550-, 650-, and 850-nm useful wavelengths. While operation in the visible spectrum is generally desired, since these are the conditions in which the eye operates, the near-infrared spectrum may offer advantages in certain applications. For example, the patient's eye may be more relaxed if the patient does not know measurement is taking place. Regardless of the wavelength of the optical radiation, power should be restricted in ophthalmic applications to eye-safe levels. For laser radiation, appropriate eye-safe exposure levels can be found in the U.S. Federal Performance Standard for Laser Products. If the analysis is to be performed on an optical system other than the eye, the examination wavelength range logically should incorporate the intended performance range of the system.

To select a small-diameter collimated core of laser light beam 14, an iris diaphragm 16 is used to block all of laser light beam 14 except for the laser beam 18 of a size desired for use. In terms of the present invention, the laser beam 18 will have a diameter in the range of approximately 0.5–4.5 mm, with 1–3 mm being typical, by way of example. A badly aberrated eye uses a smaller-diameter beam, while an eye with only slight aberrations can be evaluated with a larger-diameter beam. Depending on the output divergence of the laser 12, a lens can be positioned in the beam path to optimize collimating of the beam.

Laser beam 18, as herein described by way of example, is a polarized beam that is passed through a polarization-sensitive beam splitter 20 for routing to a focusing optical train 22, which operates to focus the laser beam 18 through the optics of the eye 120 (e.g., the cornea 126, pupil 125, and the lens 124) to the retina 122. It is to be understood that the lens 124 may not be present for a patient that has undergone a cataract procedure. However, this does not affect the present invention.

The optical train 22 images the laser beam 18 as a small spot of light at or near the eye's fovea centralis 123, where the eye's vision is most acute. Note that the small spot of light could be reflected off another portion of retina 122 in order to determine aberrations related to another aspect of one's vision. For example, if the spot of light were reflected off the area of the retina 122 surrounding the fovea centralis 123, aberrations specifically related to one's peripheral vision could then be evaluated. In all cases, the spot of light may be sized to form a near-diffraction-limited image on the retina 122. Thus the spot of light produced by laser beam 18 at fovea centralis 123 does not exceed approximately 100 μm in diameter and, typically, is on the order of 10 μm.

The diffuse reflection of the laser beam 18 back from the retina 122 is represented by solid lines 24 indicative of radiation that passes back through the eye 120. The wavefront 24 impinges on and is passed through the optical train 22 and on to the polarization-sensitive beam splitter 20. The wavefront 24 is depolarized relative to the laser beam 18 due to reflection and refraction as the wavefront 24 emanates from the retina 122. Accordingly, the wavefront 24 is turned at the polarization-sensitive beam splitter 20 and directed to a wavefront analyzer 26 such as a Hartmann-Shack (H-S) wavefront analyzer. In general, the wavefront analyzer 26 measures the slopes of wavefront 24, i.e., the partial derivatives with respect to x and y, at a number of (x,y) transverse coordinates. This partial derivative information is then used to reconstruct or approximate the original wavefront with a mathematical expression such as a weighted series of Zernike polynomials.

The polarization states for the incident laser beam 18 and the beam splitter 20 minimizes the amount of stray laser radiation reaching the sensor portion of the wavefront analyzer 26. In some situations, stray radiation may be sufficiently small when compared to the radiation returning from the desired target (e.g., the retina 122) so that the polarization specifications are unnecessary.

The present invention is able to adapt to a wide range of vision defects and as such achieves a new level of dynamic range in terms of measuring ocular aberrations. Dynamic range enhancement is accomplished with the optical train 22 and/or a wavefront sensor portion of the wavefront analyzer 26. The optical train 22 includes a first lens 220, a flat mirror 221, a Porro mirror 222, and a second lens 224, all of which lie along the path of laser beam 18 and the wavefront 24. The first lens 220 and the second lens 224 are identical lenses maintained in fixed positions. The Porro mirror 222 is capable of linear movement, as indicated by arrow 223 to change the optical path length between the lenses 220 and 224. However, it is to be understood that the present invention is not limited to the particular arrangement of the flat mirror 221 and the Porro mirror 222 and that other optical arrangements may be used without departing from the teachings and benefits of the present invention.

A "zero position" of the Porro mirror 222 is identified by replacing the eye 120 by a calibration source of collimated light to provide a reference wavefront such as a perfect plane wave 110. Such a source could be realized by a laser beam expanded by a beam telescope to the diameter that will cover the imaging plane of wavefront analyzer 26 and adjustment of the Porro mirror 222 until the wavefront analyzer 26 detects the light as being collimated. Note that the changes in optical path length brought about by the Porro mirror 222 can be calibrated in diopters to provide an approximate spherical dioptric correction.

In order to empirically determine a treatment efficiency of a particular beam profile in effecting a desired change in refraction, data were collected on the ablation of human corneas in vivo with known ablation profiles and known laser beam fluence profiles. The precision and lack of subjectivity of the above-discussed wavefront measurement was used to determine the optical results and hence the effective treatment efficiency of particular ablation profiles. Any deviations from the expected change in aberration content can be attributed to relative differences in ablation effectiveness across the corneal surface.

A single generalized ablation effectiveness function was derived from clinical data using both myopic and hyperopic nominal ablation profiles. The data were collected from nominal ablation profiles obtained using an excimer laser narrow-beam scanning spot such as that disclosed in U.S. Pat. Nos. 5,849,006 and 5,632,742, the contents of which are incorporated by reference herein.

The radially symmetric attenuation function of the present invention was determined by analysis of graphs of intended and achieved ablation depth versus normalized radial corneal position for myopic (FIG. 2) and hyperopic (FIG. 3) eyes. In its general form the ablation effectiveness function has the polynomial form $A+B\rho+C\rho^2+D\rho^3+\ldots+X\rho^n$, as described above. In a specific embodiment the function has the form $A+B\rho+C\rho^2+D\rho^3+E\rho^4$, with exemplary coefficients $A\cong0.95$, $B\cong0$, $C\cong-0.3$, $D=-0.25$, and $E=0.3$ for an optical zone radius of 3.25 mm. The ablation effectiveness function includes any radial dependence in the actual ablation rate, that is, for example, micrometers of tissue removed per pulse. However, it also incorporates any biomechanical effect or intrinsic variation in corneal optical properties that can influence the optical outcome in a radially dependent manner.

The attenuation or efficiency function is then used to modify the treatment profile by taking the desired change in corneal depth (the nominal ablation profile) and dividing this by the attenuation function. This yields a new profile that, when ablated, results in the desired change.

In a particular embodiment the attenuation is achieved by computing the Zernike description of the ablation profile and dividing the Zernike polynomial by the attenuation profile that is entered into the laser beam delivery system:

$$P_{input}(\rho,\theta)=P_{desired}(\rho,\theta)/(A+B\rho+C\rho^2+D\rho^3+\ldots+X\rho^n)$$

In a graph of a simple form of this function, $1-0.3r^2$, where $r_{max}=3.25$ mm (FIG. 4A), the radially dependent ablation efficiency varies from a value of approximately 1 proximate a central location wherein $r\cong0$ on the corneal surface to a value of approximately 0.7 at a distance from the central location wherein $r\cong3.25$ mm.

Figure 4A:
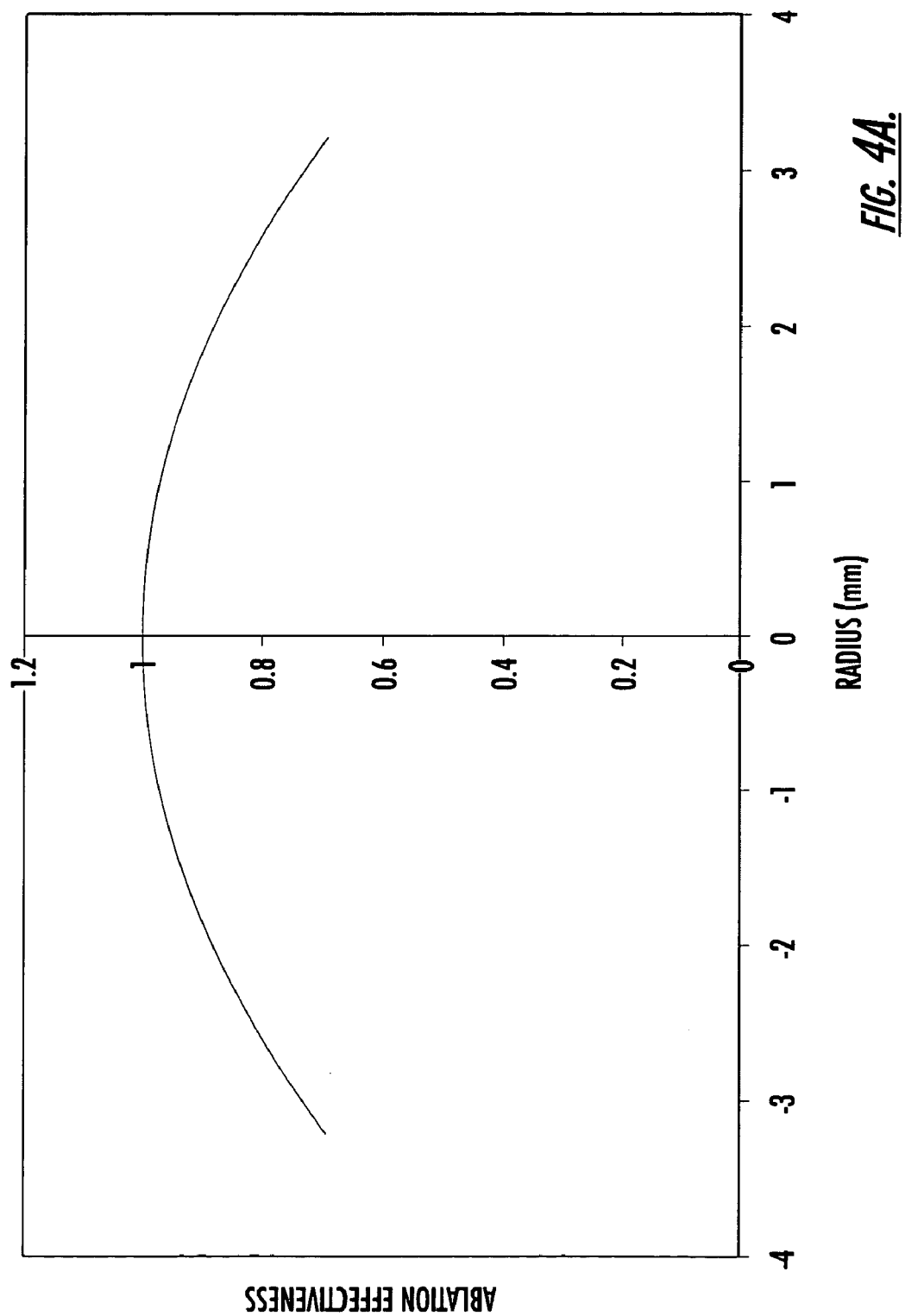
FIGS. 4A and 4B are graphs of the ablation efficiency function of the present invention.
Figure 4B:
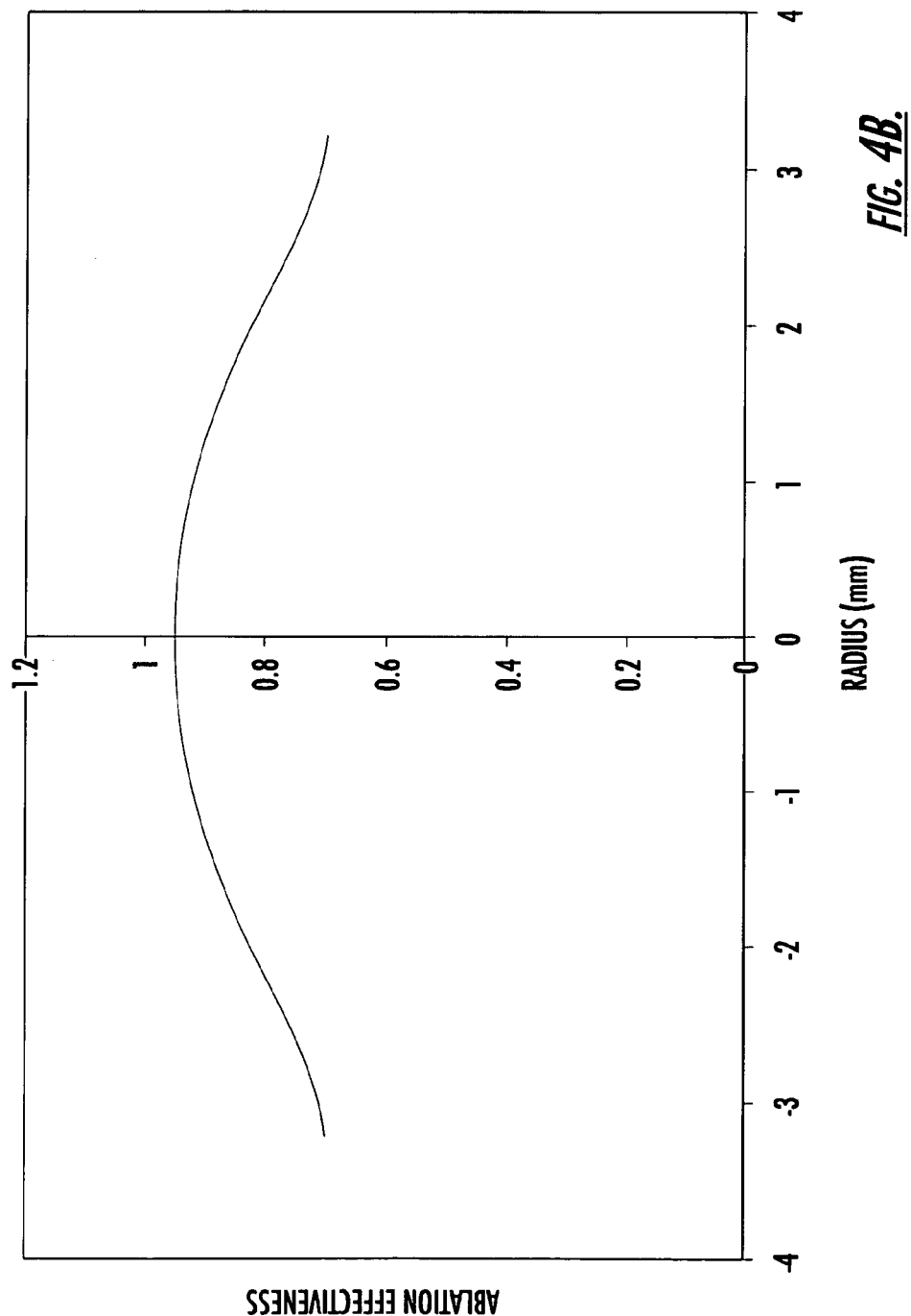

A more detailed version of the attenuation function, $0.95-0.3r^2-0.25r^3+0.3r^4$, which has a more complex shape, is shown in FIG. 4B. The specific function applied for a particular treatment laser system may depend on specifics of that device, such as beam energy, etc. Therefore, the coefficients in the attenuation function polynomial can be adjusted to optimize results for particular treatment conditions.

Preferably the optical correction is further based on refractive indices of media through which the wavefront passes. In a particular embodiment, the converter provides the path difference using a Zernike reconstruction of the wavefront, and the path difference is divided by a difference between an index of refraction of corneal material and an index of refraction of air. The optical correction is a prescribed alteration of corneal surface curvature of the eye, and the optical correction achieved by the reshaping of the corneal surface curvature of the eye is based on the prescribed alteration without regard to a resulting topography of the overall surface of the cornea.

An exemplary laser beam delivery system 5 (FIG. 5) laser beam delivery and eye tracking system may comprise, for example, that taught in U.S. Pat. No. 5,980,513, co-owned with the present application, the contents of which are incorporated herein by reference. The laser beam delivery portion of system 5 includes treatment laser source 500, projection optics 510, X-Y translation mirror optics 520, beam translation controller 530, dichroic beamsplitter 200, and beam angle adjustment mirror optics 300. The laser pulses are distributed as shots over the area to be ablated or eroded, preferably in a distributed sequence so that the desired shape of the object or cornea is achieved. Preferably the pulsed laser beam is shifted to direct the shots to a plurality of spatially displaced positions on the corneal surface to form a plurality of spatially distributed ablation spots. Each of these spots may have a predetermined diameter, for example, 2.5 or 1.0 mm, and may have an intensity distribution, for example, defined by a Gaussian or a generally flat distribution profile across the spot.

In operation of the beam delivery portion of system 5, laser source 500 produces laser beam 502 incident upon projection optics 510. Projection optics 510 adjusts the diameter and distance to focus of beam 502 depending on the requirements of the particular procedure being performed.

After exiting projection optics 510, beam 502 impinges on X-Y translation mirror optics 520, where beam 502 is translated or shifted independently along each of two orthogonal translation axes as governed by beam translation controller 530. Controller 530 is typically a processor programmed with a predetermined set of two-dimensional translations or shifts of beam 502 depending on the particular ophthalmic procedure being performed. Each of the X and Y axes of translation is independently controlled by a translating mirror.

The eye tracking portion of system 5 includes eye movement sensor 100, dichroic beamsplitter 200, and beam angle adjustment mirror optics 300. Sensor 100 determines the amount of eye movement and uses that amount to adjust mirrors 310 and 320 to track along with the eye movement. To do this, sensor 100 first transmits light energy 101-T, which has been selected to transmit through dichroic beamsplitter 200. At the same time, after undergoing beam translation in accordance with the particular treatment procedure, beam 502 impinges on dichroic beamsplitter 200, which has been selected to reflect beam 502 (e.g., a 193-nm wavelength laser beam) to beam angle adjustment mirror optics 300.

Light energy 101-T is aligned such that it is parallel to beam 502 as it impinges on beam angle adjustment mirror optics 300. It is to be understood that the term "parallel" as used herein includes the possibility that light energy 101-T and beam 502 can be coincident or collinear. Both light energy 101-T and beam 502 are adjusted in correspondence with one another by optics 300. Accordingly, light energy 101-T and beam 502 retain their parallel relationship when they are incident on eye 120. Since X-Y translation mirror optics 520 shifts the position of beam 502 in translation independently of optics 300, the parallel relationship between beam 502 and light energy 101-T is maintained throughout the particular ophthalmic procedure.

The beam angle adjustment mirror optics consists of independently rotating mirrors 310 and 320. Mirror 310 is rotatable about axis 312, as indicated by arrow 314, while mirror 320 is rotatable about axis 322, as indicated by arrow 324. Axes 312 and 322 are orthogonal to one another. In this way, mirror 310 is capable of sweeping light energy 101-T and beam 502 in a first plane (e.g., elevation), while mirror 320 is capable of independently sweeping light energy 101-T and beam 502 in a second plane (e.g., azimuth) that is perpendicular to the first plane. Upon exiting beam angle adjustment mirror optics 300, light energy 101-T and beam 502 impinge on eye 120.

The movement of mirrors 310 and 320 is typically accomplished with servo controller/motor drivers 316 and 326, respectively. In general, drivers 316 and 326 must be able to react quickly when the measured error from eye movement sensor 100 is large, and further must provide very high gain from low frequencies (DC) to about 100 radians per second to virtually eliminate both steady-state and transient error.

More specifically, eye movement sensor 100 provides a measure of the error between the center of the pupil (or an offset from the center of the pupil that the doctor selected) and the location where mirror 310 is pointed.

Light energy 101-R reflected from eye 120 travels back through optics 300 and beamsplitter 200 for detection at sensor 100. Sensor 100 determines the amount of eye movement based on the changes in reflection energy 101-R. Error control signals indicative of the amount of eye movement are fed back by sensor 100 to beam angle adjustment mirror optics 300. The error control signals govern the movement or realignment of mirrors 310 and 320 in an effort to drive the error control signals to zero. In doing this, light energy 101-T and beam 502 are moved in correspondence with eye movement while the actual position of beam 502 relative to the center of the pupil is controlled by X-Y translation mirror optics 520.

In order to take advantage of the properties of beamsplitter 200, light energy 101-T must be of a different wavelength than that of treatment laser beam 502. The light energy should preferably lie outside the visible spectrum so as not to interfere or obstruct a surgeon's view of eye 120. Further, if the present invention is to be used in ophthalmic surgical procedures, light energy 101-T must be "eye safe," as defined by the American National Standards Institute (ANSI). While a variety of light wavelengths satisfy the above requirements, by way of example, light energy 101-T may comprise infrared light energy in the 900-nm wavelength region. Light in this region meets the above-noted criteria and is further produced by readily available, economically affordable light sources. One such light source is a high pulse repetition rate GaAs 905-nm laser operating at 4 kHz, which produces an ANSI-defined eye-safe pulse of 10 nJ in a 50-ns pulse. A corneal ablation system using 193-nm ablation in a range of fluences of 100–1000 mJ/cm$^2$, which uses a small spot (<2.5 mm) may also be used. One preferred embodiment utilizes a spot <1.0 mm and 400–600 mJ/cm$^2$ peak fluences.

Thus it can be seen that this aspect of the present invention provides a system and method for providing a compensating correction function adapted to negate or cancel out the ablation efficiency function to permit the actual desired shape of the corneal removal volume to be obtained, effecting an ideal optical result.

Figure 6:
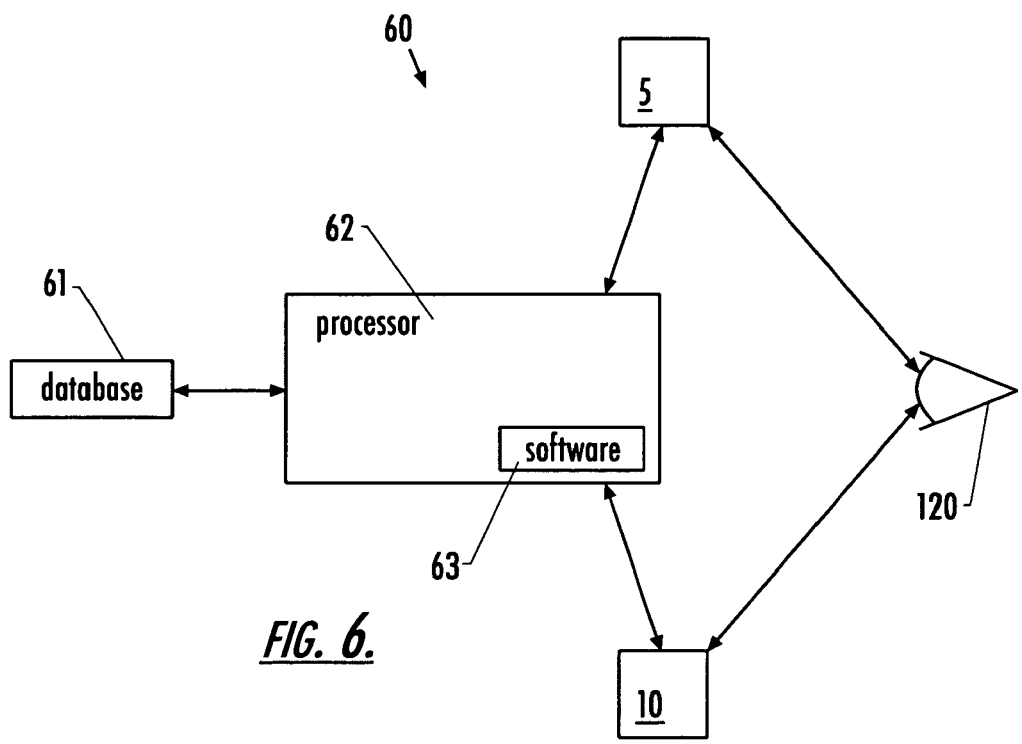
FIG. 6 is a schematic diagram of wavefront-guided treatments to incorporate target adjustments.
Figure 8A:
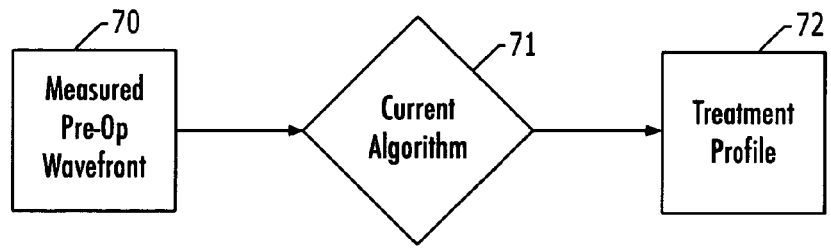
FIG. 8A (prior art) illustrates a data flow from a measured preoperative wavefront to a treatment profile.
Figure 8B:
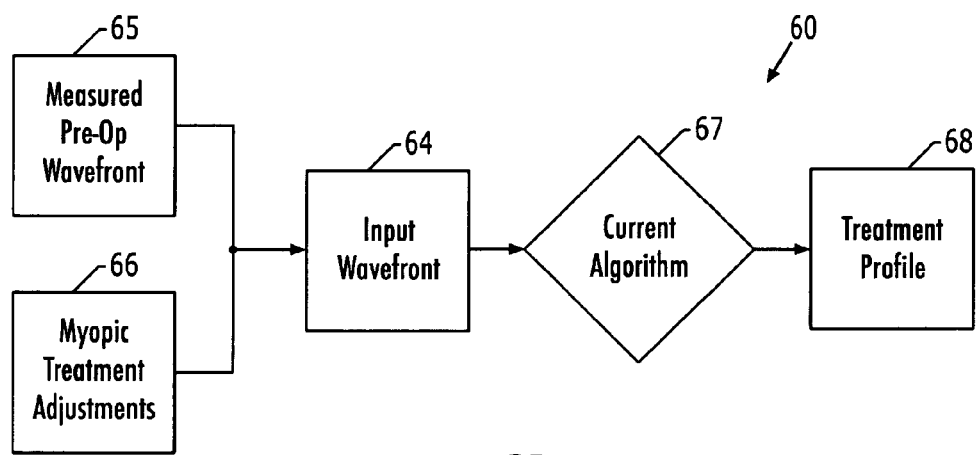
FIG. 8B illustrates a data flow from a measured preoperative wavefront and treatment adjustment data to a treatment profile.

A second embodiment of the present invention comprises a system and method for converting measured wavefront data into an ablation profile for use in corrective laser surgery on an eye 120. The data may be collected using, for example, a system 10 such as illustrated schematically in FIG. 1, although this is not intended as a limitation. The system and method are for converting the measured wavefront data into an ablation profile for correcting the measured visual defects. The ablation profile is then delivered to the eye 120 using a system 5 such as depicted in FIG. 5, although this is not intended as a limitation. The system 60 of FIGS. 6 and 8B shows how the input wavefront 64 is calculated from the measured pre-operative wavefront 65 and the treatment adjustment parameters 66, with the adjustment parameters calculated from the identified trends.

In this aspect of the invention, site-nonspecific trends have been identified by analyzing data collected pre- and post-operatively, the data having been stored in a database 61 in electronic communication with a processor 62, on which is resident a software package 63 for performing the ablation-profile calculations of the present invention. It will be understood by one of skill in the art that such a system 60 may vary with site, and that site-specific trends may be identified as above.

As discussed above, the algorithm 67 (FIG. 8B) compensates for a radially decreasing effectiveness of ablation as the treatment laser beam moves away from the corneal center to apply an appropriate aberration correction. The goal of the algorithm is to compute that modified input wavefront which, when used as the basis for the corrective laser surgery as described herein, effects a treatment profile 68 leading to an ideal optical result.

The previously discussed algorithm is used on both myopic and hyperopic corrections, and has been shown to produce good clinical results over both ranges, producing significantly less post-operative spherical aberration than previously known treatment systems. However, as the algorithm was developed for use with both types of correction, any effects unique to one of them (e.g., the post-operative healing response, biomechanical forces, etc.) may not be optimally factored into the common algorithm.

Figure 7:
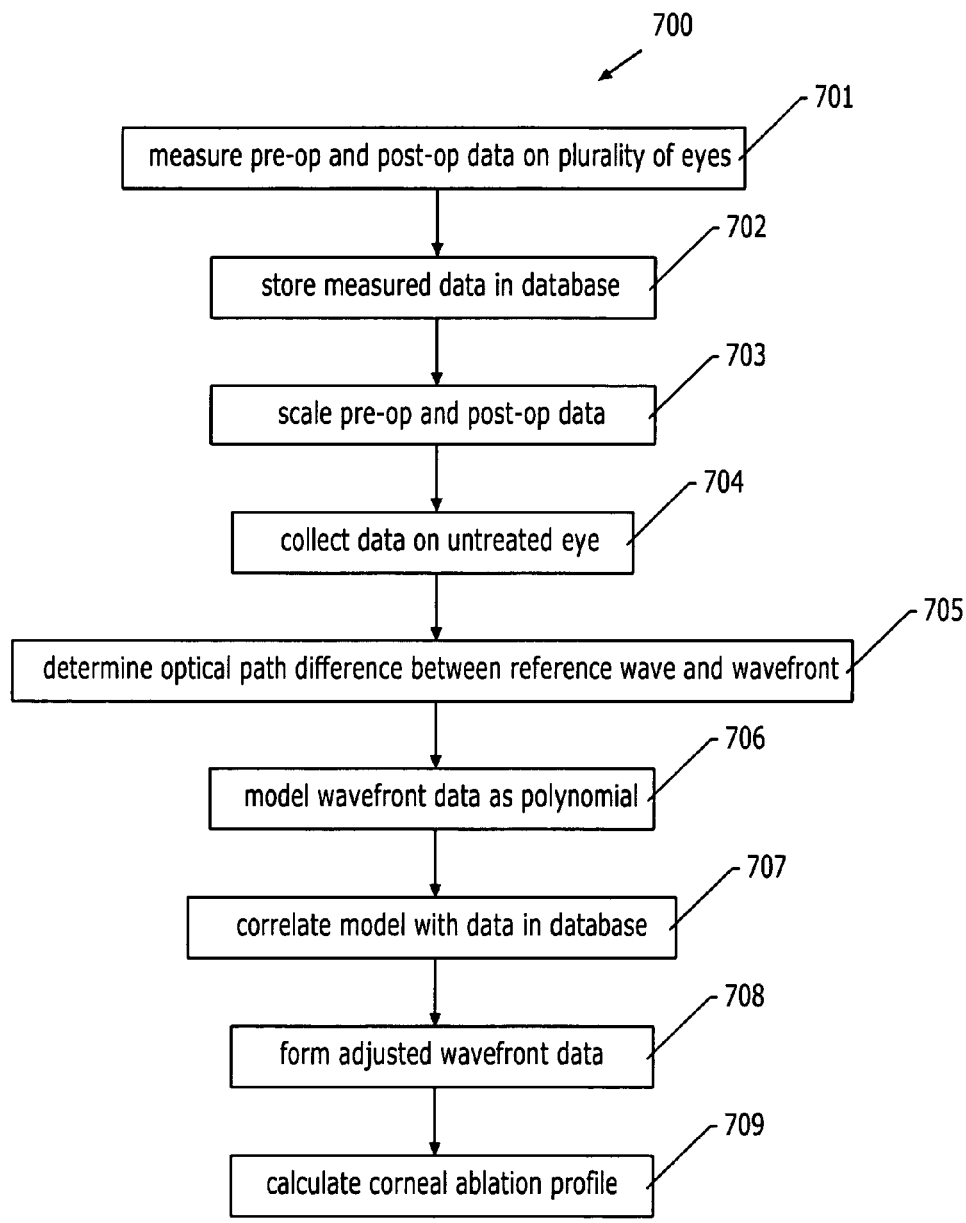
FIG. 7 is a flow chart for the method of second embodiment of the present invention.

If the effects are consistent (i.e., are not unique to a particular surgical site, microkeratome, etc.) and predictable (i.e., are accurately described by simple mathematical expressions), then a particular method 700 for addressing them is to adjust the target wavefront input into the treatment algorithm, as shown in the flowchart of FIG. 7. This method preserves the proven algorithm while at the same time automatically adding a fixed adjustment that is specific in a preferred embodiment to myopic corrections to the target wavefront to optimize myopia surgery outcomes. This is not intended as a limitation, and the system can be applied equally well to hyperopic surgery.

The method 700 comprises the steps of measuring pre-operative and post-operative wavefront data on a plurality of aberrated eyes (block 701), and storing in the database 61 the measured pre-operative and post-operative wavefront data (block 702). The pre-operative wavefront data are measured over a first radius, and the post-operative wavefront data, over a second radius smaller than the first radius.

Exemplary first and second radii comprise 3.25 and 2.5 mm, respectively, although these are not intended as limitations.

One of the sets of pre-operative data and post-operative data is then scaled to achieve a size match with the other of the pre-operative data and the post-operative data (block 703). In clinical trials, there was found to be no measurable difference between scaling up the post-operative data and scaling down the pre-operative data.

Next measured wavefront data are collected on an untreated, aberrated eye 120 (block 704). Next an optical path difference between a reference wave and the wavefront is determined (block 705). The measured wavefront data and the stored data are modeled as a polynomial comprising a plurality of coefficients (block 706). In a preferred embodiment the polynomial comprises a Zernike polynomial.

The measured wavefront data are correlated with accumulated data stored in the database 61 on previously treated eyes (block 707). Preferably each coefficient is correlated with one or more coefficients of the stored data.

Next an adjustment is applied to the measured wavefront data based upon the correlation to form adjusted wavefront data for input to a wavefront data correction algorithm (block 708). This algorithm is then used to calculate a corneal ablation profile (block 709).

The analytical methods and exemplary clinical results will now be presented with reference to FIGS. 9–15. The eyes included in the analysis comprise a myopic cohort for which three-month follow-up data were available, comprising 118 eyes from four sites. Data for each eye included wavefront measurements at the pre-operative and three-month visits, along with phoropter refractions at the same intervals.

The wavefront measurements in the exemplary embodiment are made with a device such as illustrated in FIG. 1, using a wavelength of 670 nm, although this is not intended as a limitation. Pre-operative wavefronts are reconstructed over a 3.25-mm radius, matching the optical zone of a laser ablation. Post-operative data are processed over a smaller radius, 2.5 mm, to avoid peripheral wavefront data affecting evaluation within the optical zone. To allow direct comparison of the pre- and post-operative data, one of the data sets is scaled to the unit circle size of the other data set. Both scalings were tested, and the findings were consistent over both dimensions. Herein are included results for the scaling-up of the 2.5-mm data to 3.25 mm.

The attempted change in the various Zernike terms was compared with that actually achieved at three months. All data were scaled to the optic zone radius of 3.25 mm, and then the post-operative Zernike coefficients were subtracted from the pre-operative values. The differences were analyzed against the pre-operative values, with the target for each surgery being zero residual aberrations. The attempted and achieved changes in the wavefront aberrations were analyzed statistically to identify significant correlations, either positive or negative. Each input term was checked against each output term.

In cases where a significant correlation existed between an achieved aberration change and one or more attempted aberration changes, a least-squares-fit analysis was applied to determine the optimal linear relationship. For example, if the achieved change in Zernike term $C_M$ was found to depend significantly on the attempted changes in both $C_M$ and a second aberration $C_N$, then the result of the trend analysis would be an equation describing the best-fit linear relationship:

$$\text{achieved } C_M = A(\text{attempted } C_M) + B(\text{attempted } C_N) + K$$

where A and B are best-fit linear dependencies and K is a constant offset term.

If any significant trends emerged, the data were divided into two subgroups containing the eyes from the largest group and the remaining eyes from the other four sites. The data were then reanalyzed for these two subgroups and compared with the larger combined groups, to ensure that the trends were consistent across the sites.

Figure 9:
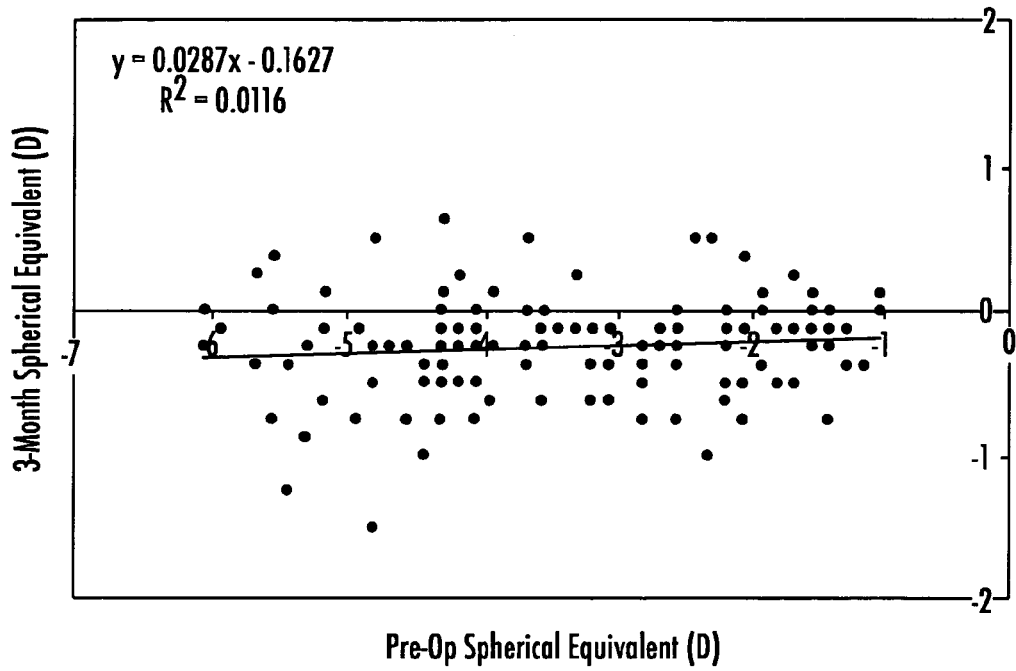
FIG. 9 is a graph of pre-operative versus post-operative refractions.

In FIG. 9 is graphed the relationship between the spherical equivalent refractions pre-operatively (abscissa) and three months post-operatively (ordinate), based on the phoropter examination, for N=118. The outcomes are not significantly correlated with the pre-operative myopia. It may be seen that the best-fit line is substantially horizontal and is slightly negatively displaced. Over the entire attempted myopic correction range there is a tendency towards slight under-correction, on average by approximately ¼ diopter. This finding persisted when the data were divided into the site subgroups, as shown in Table 1. While this difference is small, it is believed that customized treatments can be improved if the target myopic correction in the wavefront is increased by ¼ diopter.

TABLE 1

Comparison of Pre- and Post-Op SE Refractions for Different Sites.

| Data Group | Average SE Refraction Pre-OP (D) | Average SE Refraction at 3 Months (D) |
|---|---|---|
| All Eyes (N = 118) | −3.38 | −0.26 |
| Waterloo (N = 62) | −3.31 | −0.20 |
| Other Sites (N = 56) | −3.47 | −0.32 |

In comparing the attempted versus achieved changes in the various wavefront aberrations, significant findings comprise:

Linear regression analysis showed a high degree of correlation between attempted and achieved corrections of each of the second-order wavefront aberrations (i.e., defocus, oblique primary astigmatism, and horizontal/vertical primary astigmatism—$C_3$, $C_4$, and $C_5$).

For the $C_5$ term, which corresponds to horizontal/vertical astigmatism, there was a consistent small offset (i.e., a small constant term in the best-fit linear relationship).

Achieved changes in all third-order aberrations (spherical aberration, oblique secondary astigmatism, and horizontal/vertical secondary astigmatism—$C_6$ through $C_9$), as well as the two "tetrafoil" fourth-order aberrations ($C_{13}$ and $C_{14}$) were all positively correlated with the attempted change in each, although the correlation coefficients were smaller than those seen with the second-order terms.

Achieved changes in the three remaining aberrations ($C_{10}$, $C_{11}$, and $C_{12}$) were unique in that they were significantly correlated with attempted changes in other aberrations ($C_3$, $C_4$, and $C_5$, respectively), as well as themselves.

No other aberrations exhibited a significant cross-correlation.

Figure 10:
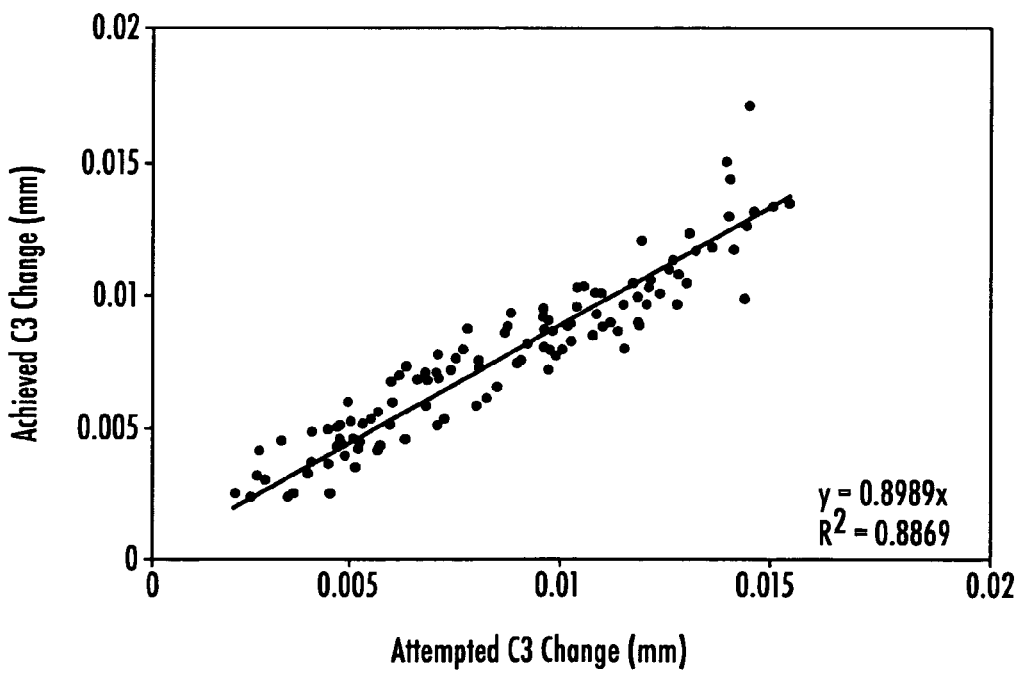
FIG. 10 is a graph of attempted versus achieved defocusing correction.

FIG. 10 graphs the relationship between the attempted versus achieved defocus correction ($C_3$). For all 118 eyes the achieved change is on average 89.89% of that attempted, with a high degree of correlation. This finding also existed when the data were divided into the two subgroups, as shown in Table 2.

TABLE 2

Linear Regression Analysis of Defocus Wavefront Error Correction.

| Data Group | Best Fit Linear Slope | Correlation Coefficient |
|---|---|---|
| All Eyes (N = 118) | 0.8989 | +0.943 |
| Waterloo (N = 62) | 0.8915 | +0.961 |
| Non-Waterloo (N = 56) | 0.9073 | +0.929 |

Figure 11:
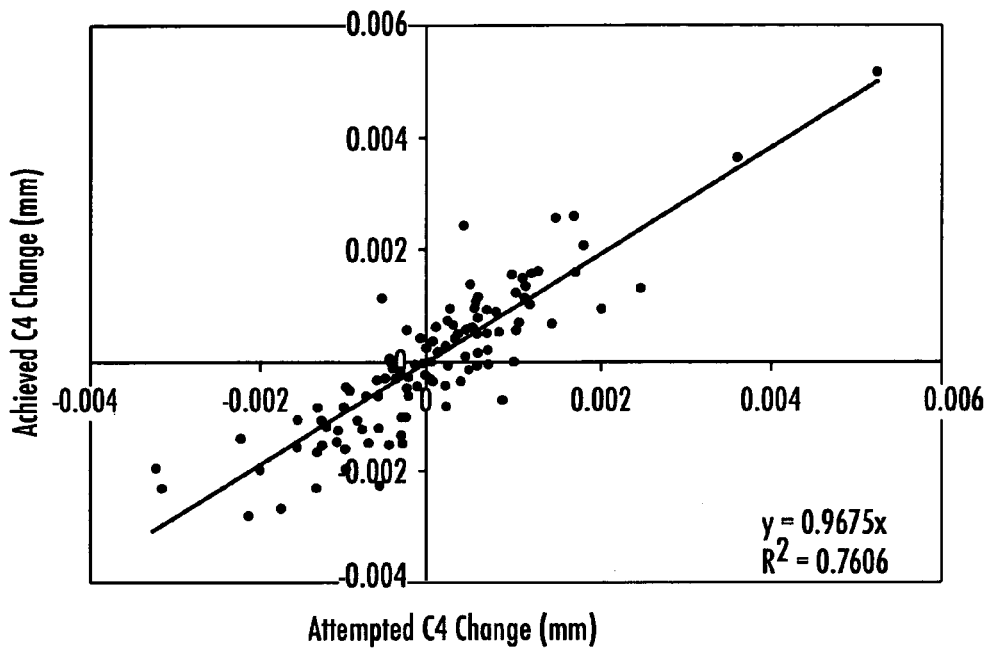
FIG. 11 is a graph of attempted versus achieved oblique astigmatism correction.

FIG. 11 graphs the attempted versus achieved correction of the oblique astigmatic aberration ($C_4$), again for N=118. On average 97% of the attempted correction was achieved. There was a small difference in this percentage correction for the different subgroups, as shown in Table 3.

TABLE 3

Linear Regression Analysis of Oblique Astigmatism Correction.

| Data Group | Best Fit Linear Slope | Correlation Coefficient |
|---|---|---|
| All Eyes (N = 118) | 0.9675 | +0.8732 |
| Waterloo (N = 62) | 0.8767 | +0.8566 |
| Non-Waterloo (N = 56) | 1.0564 | +0.8952 |

Figure 12:
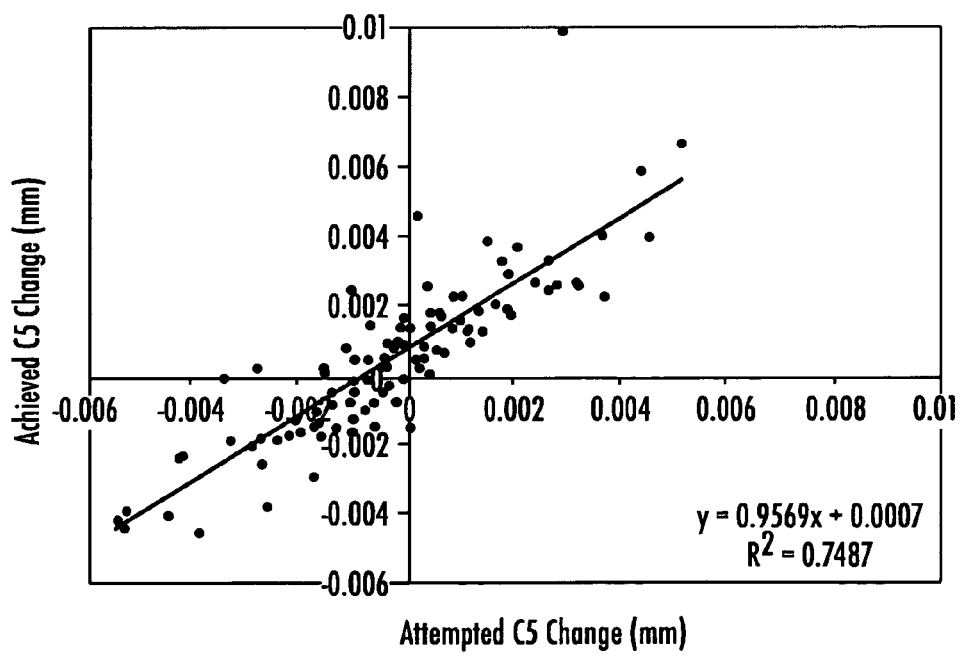
FIG. 12 is a graph of attempted versus achieved horizontal/vertical astigmatism correction.

FIG. 12 graphs the relationship between attempted and achieved correction of horizontal/vertical astigmatism ($C_5$), again for N=118. While the slope is again near unity and the correction fairly high, there exists a finite offset in the linear regression line. This finding was consistently observed in the subgroup analysis, as shown in Table 4.

TABLE 4

Linear Regression Analysis of Horizontal/Vertical Astigmatism Wavefront Error Correction.

| Data Group | Best Fit Linear Slope | Offset | Correlation Coefficient |
|---|---|---|---|
| All Eyes (N = 118) | 0.9569 | +0.000684 | +0.8653 |
| Waterloo (N = 62) | 0.9808 | +0.000430 | +0.9305 |
| Non-Waterloo (N = 56) | 0.9540 | +0.000967 | +0.8319 |

Figure 13:
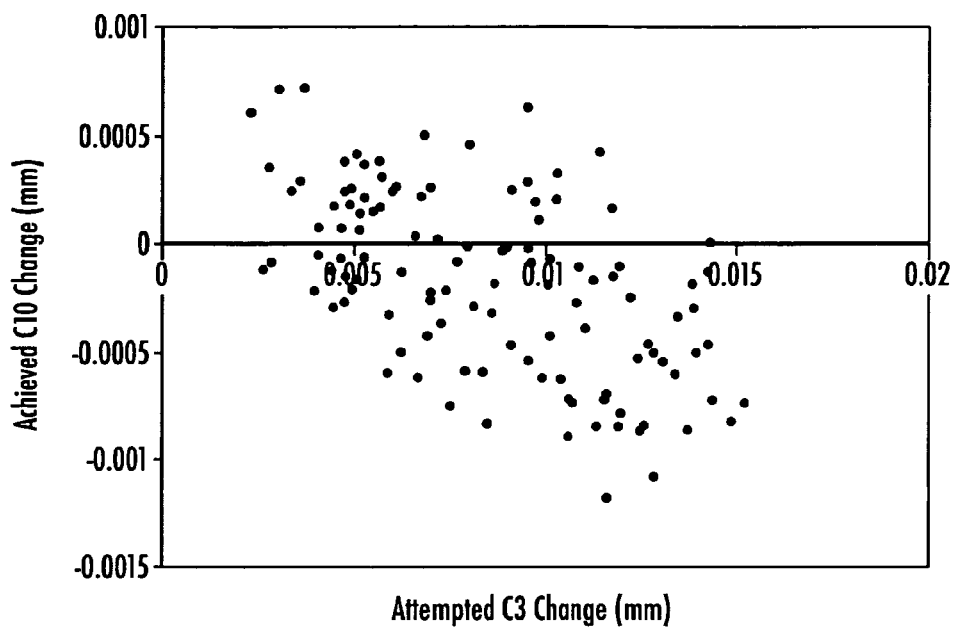
FIG. 13 is a graph of attempted defocus correction versus achieved spherical aberration correction.

The achieved change in the spherical aberration term ($C_{10}$) was positively correlated with the attempted spherical aberration correction, but even more positively correlated with the attempted defocus correction. The latter relationship is shown in FIG. 13, with N=118. The best correlation relationships for the different subgroups are shown in Table 5.

TABLE 5

Linear Regression Analysis of Spherical Aberration Correction.

| Data Group | Attempted $C_{10}$ Dependence | Attempted $C_3$ Dependence | Correlation Coefficient |
|---|---|---|---|
| All Eyes (N = 118) | 0.6471 | −0.0491 | +0.6775 |
| Waterloo (N = 62) | 0.6520 | −0.0533 | +0.7235 |
| Non-Waterloo (N = 56) | 0.6336 | −0.0441 | +0.6322 |

Figure 14:
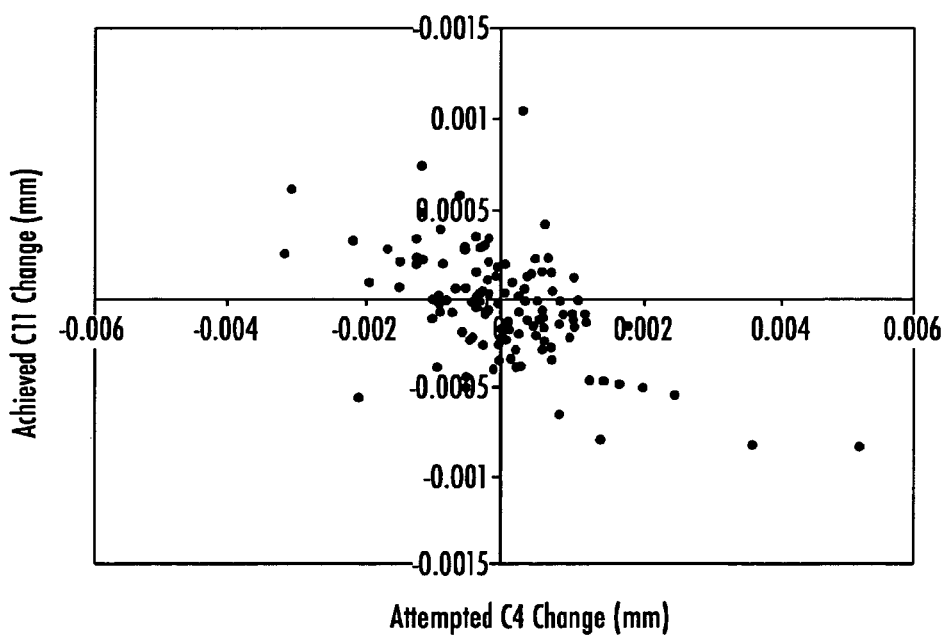
FIG. 14 is a graph of attempted oblique primary astigmatism correction versus achieved oblique secondary astigmatism correction.

The achieved change in the oblique secondary astigmatism term ($C_{11}$) was most positively correlated with the attempted change in primary oblique astigmatism ($C_4$), as shown in FIG. 14, followed by the attempted $C_{11}$ change. Regression coefficients for the relationship are shown in Table 6.

TABLE 6

Regression Analysis of Oblique Secondary Astigmatism.

| Data Group | Attempted $C_{11}$ Dependence | Attempted $C_4$ Dependence | Correlation Coefficient |
|---|---|---|---|
| All Eyes (N = 118) | 0.4873 | −0.1751 | +0.5884 |
| Waterloo (N = 62) | 0.4490 | −0.1807 | +0.6437 |
| Non-Waterloo (N = 56) | 0.5376 | −0.1703 | +0.5469 |

Figure 15:
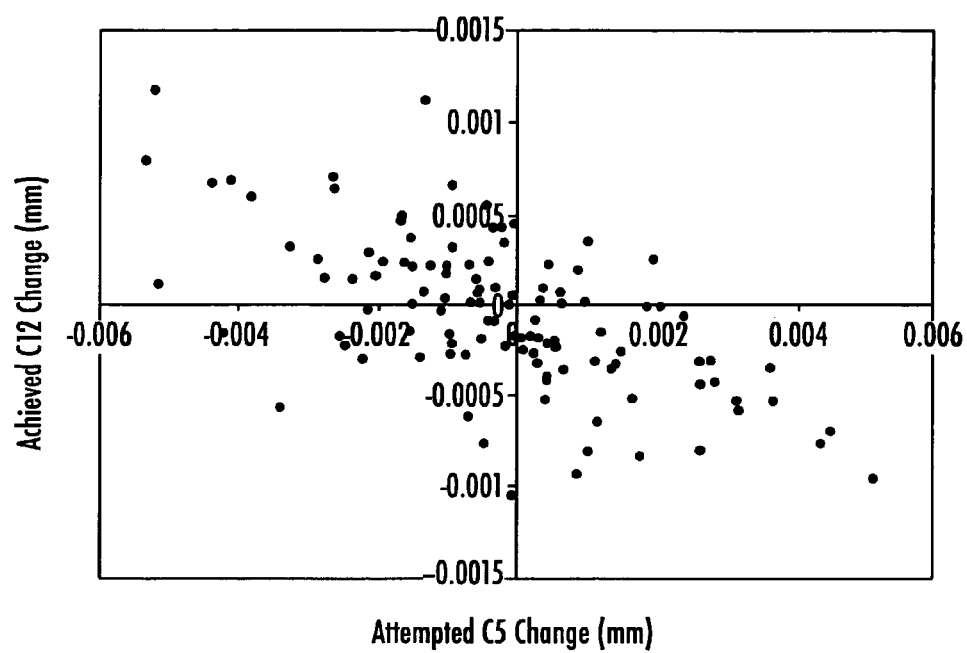
FIG. 15 is a graph of attempted horizontal/vertical primary astigmatism correction versus achieved horizontal/vertical secondary astigmatism correction.

The achieved change in the horizontal/vertical secondary astigmatism term ($C_{12}$) was most positively correlated with the attempted change in primary horizontal/vertical astigmatism ($C_5$), as shown in FIG. 15, followed by the attempted $C_{12}$ change. Regression coefficients for the combined relationship are shown in Table 7. A small negative offset was also seen.

TABLE 7

Regression Analysis of Horizontal/Vertical Secondary Astigmatism.

| Data Group | Attempted $C_{12}$ Dependence | Attempted $C_5$ Dependence | Offset | Correlation Coefficient |
|---|---|---|---|---|
| All Eyes (N = 118) | 0.7468 | −0.1460 | −0.000116 | +0.6991 |
| Waterloo (N = 62) | 0.6150 | −0.1372 | −0.000041 | +0.6787 |
| Non-Waterloo (N = 56) | 0.8715 | −0.1588 | −0.000201 | +0.7473 |

The general mathematical approach used to develop the targeting equations is as follows. Consider a conclusive trend between the attempted change in a particular aberration (attempted $C_N$) and the achieved change in that term (achieved $C_N$):

$$\text{achieved } C_N = a(\text{attempted } C_N) + b \quad (1)$$

This means that:

$$\text{attempted } C_N = [(\text{achieved } C_N) - b]/a \quad (2)$$

If the objective is to make the achieved change equal to the measured wavefront error (measured $C_N$), then the target value input into the treatment algorithm (target $C_N$) is:

$$\text{target } C_N = [(\text{measured } C_N) - b]/a \quad (3)$$

For the higher-order terms, where the achieved aberration change is linked to more than one attempted parameter, a conservative mathematical approach is taken. The starting equation is analogous to Eq. (1):

$$\text{achieved } C_N = a(\text{attempted } C_N) + c(\text{attempted } C_X) + b$$

which leads to:

$$\text{attempted } C_N = [(\text{achieved } C_N) - c(\text{attempted } C_X) - b]/a$$

However, for all three of the higher-order aberrations under consideration, the uncertainty in a is larger than that of c. In all three cases a is a positive number less than 1, which results in an increase in attempted $C_N$. It is set equal to 1 to keep the change in the coefficient relatively modest. From this point the logic is the same as is used to generate Eq. (3). The final targeting functions that are used for treatment are, based upon a 3.25-mm unit circle radius:

target $C_3$=1.11(measured $C_3$)+0.000714     (1)

target $C_4$=1.03(measured $C_4$)     (2)

target $C_5$=1.04(measured $C_5$)+0.000715     (3)

target $C_{10}$=(measured $C_{10}$)+0.055(measured $C_3$)+ 0.000035     (4)

target $C_{11}$=(measured $C_{11}$)+0.18(measured $C_4$)     (5)

target $C_{12}$=(measured $C_{12}$)+0.15(measured $C_5$)     (6)

The offset in (1) corresponds to approximately ¼ diopter of defocus error over a 3.25-mm unit circle radius. The offset in (3) corresponds to the same amount of mixed astigmatism. The offset in (4) exists because of the offset in (1); that is, a small fraction of the defocus offset carries through to the higher-order relationship. No offset exists in (6) because the offset in the trend for $C_{12}$ was negated by the carry-through offset from (3).

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

That which is claimed is:

1. A method for converting measured wavefront data into an ablation profile for correcting visual defects, the method comprising the steps of:
   providing measured wavefront data on an aberrated eye of a first patient;
   correlating the measured wavefront data with accumulated data on previously treated eyes of a plurality of patients; and
   applying an adjustment to the measured wavefront data based upon the correlating step to form adjusted wavefront data for input to a wavefront data correction algorithm to calculate a corneal ablation profile therefrom.

2. The method recited in claim 1, wherein the wavefront data providing step comprises analyzing a wavefront emanating from the eye and determining an optical path difference between a reference wave and the wavefront.

3. The method recited in claim 1, further comprising the steps, prior to the correlating step, of:
   storing in a database measured pre-operative wavefront data on a plurality of aberrated eyes;
   storing in the database measured post-operative wavefront data on the plurality of aberrated eyes following corneal ablation corrective treatment; and wherein:
   the correlating step comprises accessing accumulated data from the database.

4. The method recited in claim 3, further comprising the steps, prior to the storing steps, of measuring pre-operative and post-operative wavefront data.

5. The method recited in claim 1, further comprising the step of modeling the measured wavefront data as a polynomial comprising a plurality of coefficients, and wherein the correlating step comprises correlating each coefficient with a respective coefficient of the accumulated data, the accumulated data comprising polynomials, each comprising a plurality of coefficients.

6. The method recited in claim 5, wherein the polynomial comprises a Zernike polynomial.

7. The method recited in claim 1, wherein the wavefront correction algorithm is adapted for correcting an eye characterized by at least one of myopia, hyperopia, and being dominated by higher-order aberrations.

8. The method recited in claim 1, wherein the adjustment is substantially site-independent.

9. The method recited in claim 1, wherein the adjustment is site-dependent.

10. A method for converting measured wavefront data into an ablation profile for correcting visual defects, the method comprising the steps of:
    providing measured wavefront data on an aberrated eye;
    measuring pre-operative wavefront data over a first radius and measuring post-operative wavefront data over a second radius smaller than the first radius;
    storing in a database measured pre-operative wavefront data on a plurality of aberrated eyes;
    storing in the database measured post-operative wavefront data on the plurality of aberrated eyes following corneal ablation corrective treatment;
    accessing accumulated data from the database;
    correlating the measured wavefront data with accumulated data on previously treated eyes; and
    applying an adjustment to the measured wavefront data based upon the correlating step to form adjusted wavefront data for input to a wavefront data correction algorithm to calculate a corneal ablation profile therefrom.

11. The method recited in claim 10, further comprising the step, following the measuring steps, of scaling one of the pre-operative data and the post-operative data to achieve a size match with the other of the pre-operative data and the post-operative data.

12. A method of performing a refractive correction on a cornea of an eye, the method comprising the steps of:
    providing measured wavefront data on an aberrated eye of a first patient;
    correlating the measured wavefront data with accumulated data on previously treated eyes of a plurality of patients;
    applying an adjustment to the measured wavefront data based upon the correlating step to form adjusted wavefront data for input to a wavefront data correction algorithm to calculate a corneal ablation profile therefrom;
    directing a laser beam onto the first patient eye for ablating the cornea; and
    moving the laser beam in a pattern about the first patient eye, the pattern based on the corneal ablation profile.

13. A system for converting measured wavefront data into an ablation profile for correcting visual defects comprising:
    a processor; and
    software resident on the processor having code segments adapted to:
    correlate measured wavefront data on an eye of a first patient with accumulated data on a plurality of previously treated eyes; and
    apply an adjustment to the measured wavefront data based upon the correlating step to form adjusted wavefront data for input to a wavefront data correction algorithm to calculate a corneal ablation profile therefrom for application to the first patient eye.

14. The system recited in claim 13, wherein the software further has a code segment adapted to apply the wavefront data correction algorithm.

15. The system recited in claim 13, wherein the software further has a code segment adapted to determine an optical path difference between a reference wave and the wavefront.

16. The system recited in claim 13, wherein the measured wavefront data comprise pre-operative wavefront data measured over a first radius and post-operative wavefront data measured over a second radius smaller than the first radius, the pre-operative wavefront data and the post-operative wavefront data scaled to achieve a size match therebetween.

17. The system recited in claim 13, wherein the software further has a code segment adapted to model the measured wavefront data as a polynomial comprising a plurality of coefficients, and wherein the correlation comprises correlating each coefficient with at least one coefficient of the accumulated data, the accumulated data comprising polynomials, each comprising a plurality of coefficients.

18. The system recited in claim 17, wherein the polynomial comprises a Zernike polynomial.

19. The system recited in claim 13, wherein the wavefront data correction algorithm is adapted for correcting an eye characterized by at least one of myopia, hyperopia, and being dominated by higher-order aberrations.

20. The system recited in claim 13, wherein the adjustment is substantially site-independent.

21. The system recited in claim 13, wherein the adjustment is site-dependent.

* * * * *